US011873222B2

United States Patent
Li

(10) Patent No.: US 11,873,222 B2
(45) Date of Patent: Jan. 16, 2024

(54) HIGHLY METALLIC, HYDROPHILIC, POLYMER-FREE CARBON NANOTUBE (CNT) THIN SHEET AND USES THEREOF

(71) Applicant: 4th Phase Technologies, Inc., Wilmington, DE (US)

(72) Inventor: Chunhong Li, West Chester, PA (US)

(73) Assignee: 4th Phase Technologies, Inc., Wilmington, DE (US)

( * ) Notice: Subject to any disclaimer, the term of this patent is extended or adjusted under 35 U.S.C. 154(b) by 684 days.

(21) Appl. No.: 16/947,364

(22) Filed: Jul. 29, 2020

(65) Prior Publication Data
US 2021/0032109 A1    Feb. 4, 2021

Related U.S. Application Data

(60) Provisional application No. 62/879,865, filed on Jul. 29, 2019.

(51) Int. Cl.
| | |
|---|---|
| *B32B 9/00* | (2006.01) |
| *C01B 32/168* | (2017.01) |
| *B01J 20/20* | (2006.01) |
| *B01J 20/30* | (2006.01) |
| *C12M 1/00* | (2006.01) |
| *B01D 71/02* | (2006.01) |
| *C02F 1/44* | (2023.01) |
| *H05K 9/00* | (2006.01) |
| *B01D 53/22* | (2006.01) |
| *B82Y 40/00* | (2011.01) |
| *B82Y 30/00* | (2011.01) |

(52) U.S. Cl.
CPC .......... *C01B 32/168* (2017.08); *B01D 53/228* (2013.01); *B01D 71/021* (2013.01); *B01J 20/205* (2013.01); *B01J 20/3085* (2013.01); *C02F 1/44* (2013.01); *C12M 23/20* (2013.01); *H05K 9/0081* (2013.01); *B82Y 30/00* (2013.01); *B82Y 40/00* (2013.01); *C01B 2202/22* (2013.01); *C01P 2004/03* (2013.01); *Y10T 428/30* (2015.01)

(58) Field of Classification Search
CPC ... Y10T 428/30; C01B 32/156; C01B 32/168; B82Y 30/00; B82Y 40/00
USPC .......................................... 428/408; 423/448
See application file for complete search history.

(56) References Cited

U.S. PATENT DOCUMENTS

2005/0263456 A1* 12/2005 Cooper ................. A61L 2/0082
                                                     210/660

FOREIGN PATENT DOCUMENTS

KR          101726823     *    4/2017

* cited by examiner

*Primary Examiner* — Daniel H Miller
(74) *Attorney, Agent, or Firm* — Ryan L. Marshall; Barnes & Thornburg LLP

(57) ABSTRACT

The present disclosure is directed to the preparation of highly metallic, hydrophilic, polymer-free carbon nanotube (CNT) thin sheets with high tensile strength. The densified CNT sheet has reduced pore sizes, increased tensile strength, and improved electrical conductivity. The disclosed CNT materials can be used as filtration membranes with little or no propensity toward surface fouling. Such densified CNT sheets are also useful as superior electromagnetic interference (EMI) shielding materials.

20 Claims, 10 Drawing Sheets

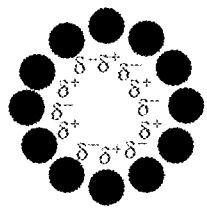 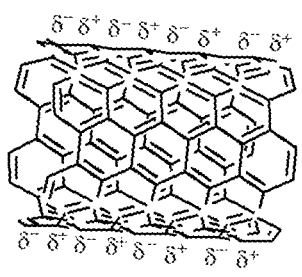 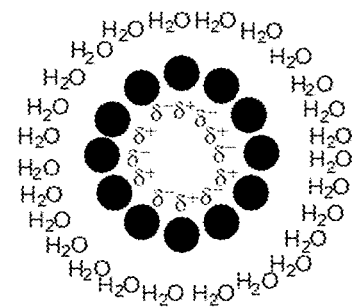
FIG. 1 (A)    FIG. 1 (B)    FIG. 1 (C)
FIG. 1

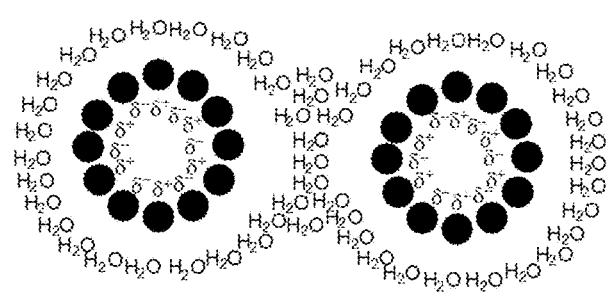 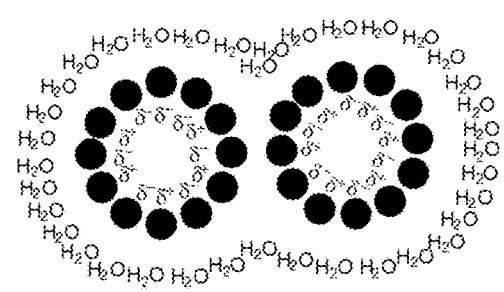
FIG. 2 (A)　　　　　　　　　　FIG. 2 (B)
FIG. 2

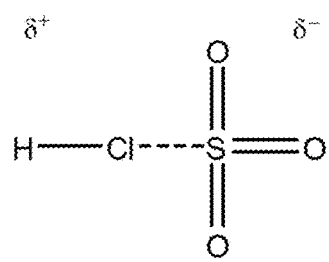 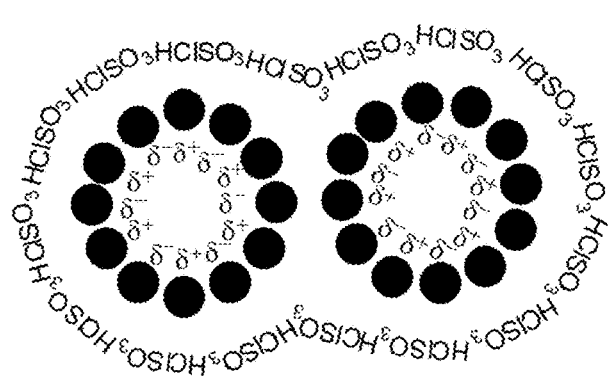
FIG. 3 (A)            FIG. 3 (B)
FIG. 3

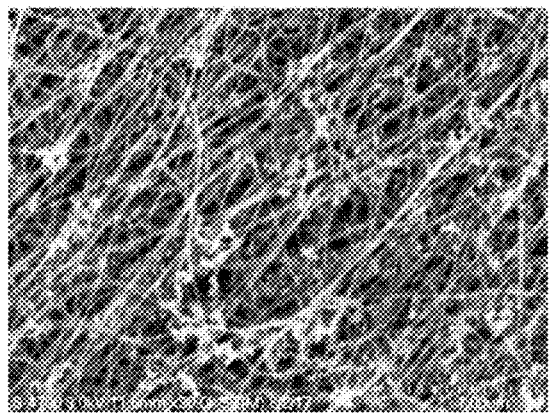 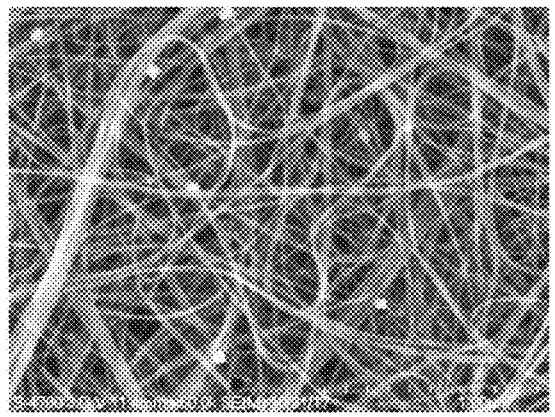
FIG. 4 (A)  FIG. 4 (B)
FIG. 4

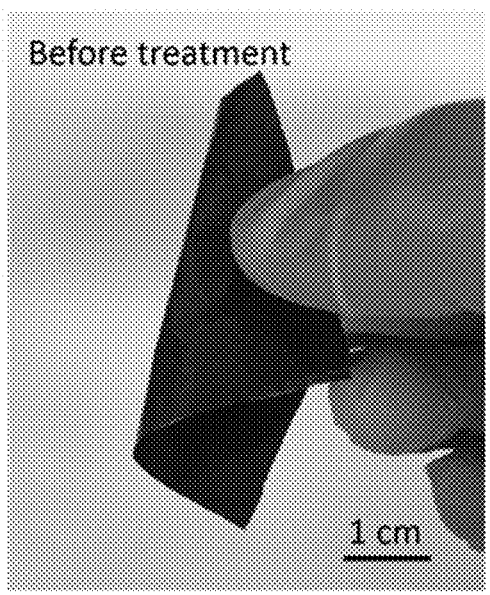 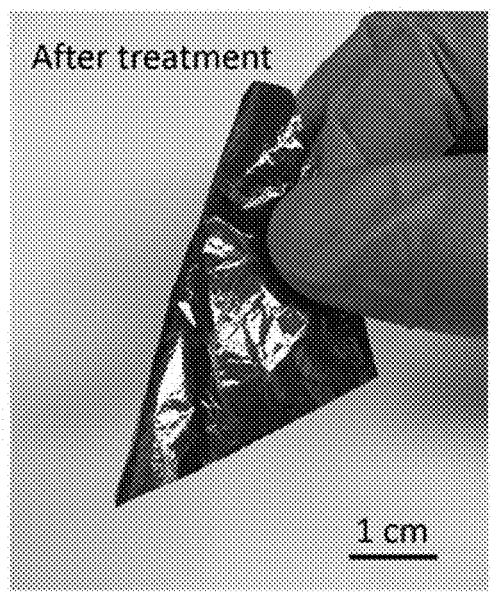
FIG. 5 (A)  FIG. 5 (B)
FIG. 5

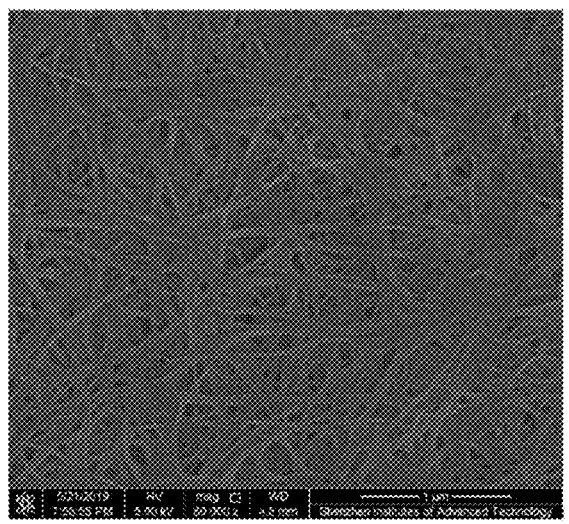 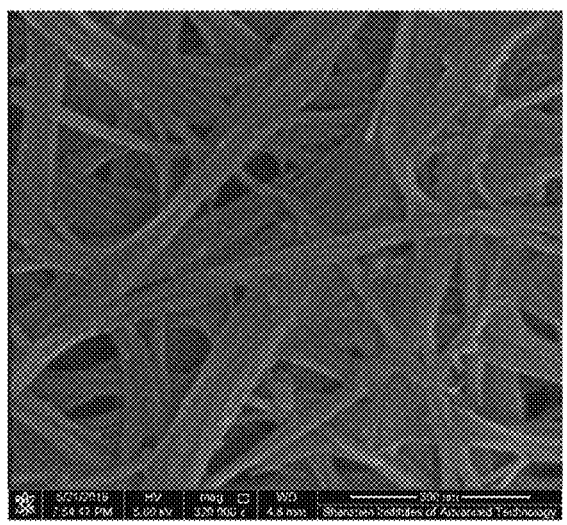
FIG. 6 (A)　　　　　　　　FIG. 6 (B)
FIG. 6

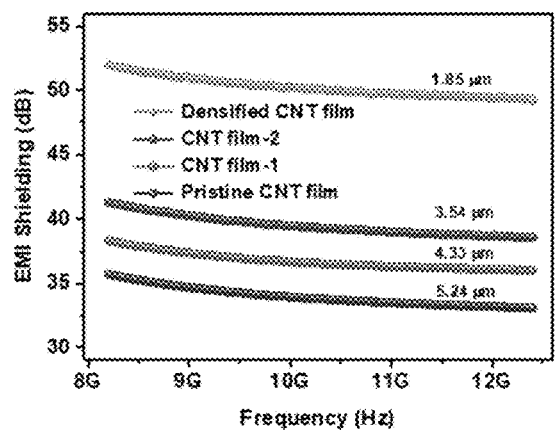
FIG. 9 (A)
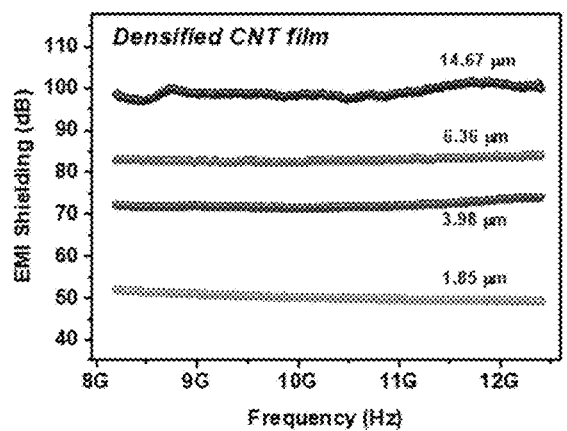
FIG. 9 (B)
FIG. 9

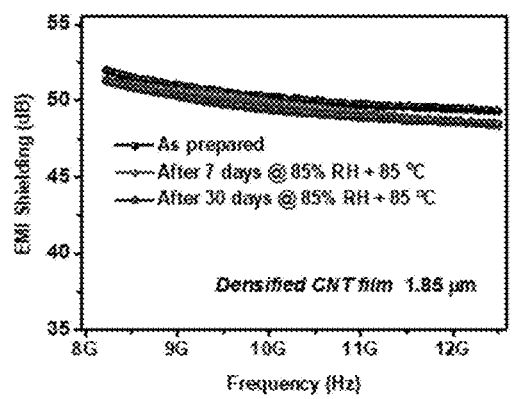 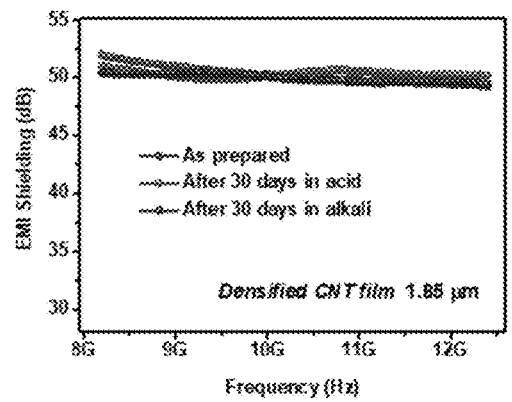
FIG. 10 (A)    FIG. 10 (B)
FIG. 10

HIGHLY METALLIC, HYDROPHILIC, POLYMER-FREE CARBON NANOTUBE (CNT) THIN SHEET AND USES THEREOF

TECHNICAL FIELD

The present disclosure generally relates to highly metallic, hydrophilic, polymer-free carbon nanotube (CNT) thin sheets and methods of their preparation. Highly metallic, hydrophilic, polymer-free CNT thin sheet materials are useful as filtration membranes with little or no propensity toward surface fouling and are also useful as superior electromagnetic interference (EMI) shielding materials.

BACKGROUND

Individual CNTs are promising candidates for many applications due to their unique properties including mechanical strength, chemical stability, and resistance to both high temperatures and organic solvents. Being pliable and lightweight, they also conduct electricity and heat. However, it is difficult to transfer these properties of individual CNTs into a large-area CNT sheet.

CNT powders have been used to prepare polymer composite thin films, in which CNT powders are dispersed or chemically functionalized in solvents and mixed with polymers. It is typically difficult to uniformly functionalize CNTs due to the presence of variable amounts of amorphous carbon and the variable degree of aggregation and bundling. Covalent CNT functionalization relies on harsh chemical treatments, which further damage CNT surface structure, or by physical means such as sonication, which tends to help disperse CNTs into solvents but further damages CNT structure. The degree and uniformity of CNT powder dispersion is also difficult to control.

Composite films invariably have the limitations of the polymers. For example, many composite films lack the chemical stability and mechanical strength of CNTs in the absence of the polymer. Degradation of polymers in CNT composite films can also lead to the leaching of degradation products and CNTs over time, which is a health and safety concern.

Preparing CNT thin films of sufficient tensile strength in the absence of polymer binder is a challenging task. Bucky paper is one example of a CNT thin film prepared from dispersed CNT powder without the use of polymer binder. Bucky paper, however, is typically flimsy and lacks the required physical strength for many applications due to film fracture and the loss of CNTs from the film.

DexMat, Inc. has succeeded in preparing durable CNT films/tapes from CNT powder without using conventional polymer as binder. The process requires dissolving CNT powder in chlorosulfonic acid and then extruding the solution to yield aligned CNT fibers and films. The technology is most suitable to produce CNT wires, yarns and narrow tapes (<=4 cm wide) with thicknesses ranging from 10 μm to 100 μm.

Another method of producing CNT sheet without the use of polymer binder is floating catalyst chemical vapor deposition (FCCVD). In FCCVD process, pristine CNTs grown in situ in a high temperature furnace (ca. 1000-1200° C.) are deposited on a substrate surface, then physically compressed to form a sheet. At present, only a few companies can produce such pristine CNT sheets of 1 m×1 m and larger in size. Nanocomp Technologies Inc. and Suzhou Creative Nano Carbon Co., Ltd are two companies with such capability.

However, pristine CNT sheets have variable amounts of amorphous carbon along individual CNT surfaces and air pockets. The crystallinity, diameter and length of pristine CNTs in as-grown CNT sheets can also vary. The inconsistency in CNT quality presents variations in CNT sheet properties, e.g., irreproducible hydrophobicity, poor electric conductivity and poor tensile strength.

$\pi$-$\pi$ interactions and van der Waals forces exist between adjacent CNTs. However, such attractive forces between pristine CNTs is significantly compromised by the presence of amorphous carbon and air. When physically pressed together, the resulting pristine CNT sheets generally lack the required tensile strength and hydrophilicity. The pore sizes within the sheets are also difficult to control. Without the required tensile strength, pristine thin CNT sheets are invariably susceptible to film fracture and CNT loss. Thus, a process is urgently needed to make thin CNT sheets that have the requisite physical (tensile) strength with no CNT loss. Without the use of polymer as binder, such pure CNT sheets can withstand high temperature and are resistant to fouling, corrosion, degradation, and organic solvents. As a result, they will find applications in many challenging conditions where conventional membranes generally fail.

SUMMARY

In one aspect, a process for producing a purified carbon nanotube (CNT) sheet, is disclosed and includes inserting a CNT sheet into an inert atmosphere; heating the CNT sheet to an elevated temperature; and cooling the CNT sheet to an ambient temperature. In some embodiments, the elevated temperature is between about 800 and about 1200° C. In some embodiments, the inert atmosphere comprises 1% to about 5% hydrogen.

In another aspect, a process to densify carbon nanotubes (CNTs) in CNT sheet is disclosed and includes contacting a CNT sheet with a solution comprising a protic acid; rinsing the CNT sheet with a volume of protic solvent; and removing the protic solvent.

In another aspect, a process to densify carbon nanotubes (CNTs) in CNT sheet is disclosed and includes melting $SO_3$ $NEt_3$ complex on a CNT sheet; rinsing the CNT sheet with a protic solvent; removing the protic solvent.

In some embodiments, the process includes contacting the CNT sheet with $HClSO_3$.

In another aspect, a densified CNT sheet is disclosed when made from the disclosed processes.

In another aspect, a method of shielding an article from electromagnetic radiation is disclosed and includes covering an article with a densified CNT sheet.

In another aspect, a method of filtering a fluid is disclosed and includes passing the fluid through a CNT sheet. In some embodiments, the fluid is water. In some embodiments, the fluid is a gas.

In another aspect, a method of protecting a surface from corrosion is disclosed and includes covering a surface of an object with a densified CNT sheet and contacting the surface with a corrosive material. In some embodiments, the corrosive material is a protic acid or an alkaline solution. A method of protecting a surface from fouling is also disclosed and includes covering a surface of an object with a densified CNT sheet and contacting the surface with a fouling material. In some embodiments, the fouling material is a fermentation solution or a biological culture, or a heat exchange fluid.

BRIEF DESCRIPTION OF THE DRAWINGS

FIG. 1 (A) Cross-sectional view of alternating positive and negative charges (or partial charges) across an individual CNT surface (only one molecular layer is shown for brevity); (B) Alternating charge distribution along a CNT surface; (C) Formation of a thin, orderly layer of water around individual CNT due to charge separation on CNT surface (only one molecular layer is shown for brevity). A nanometer gap exists between CNT surface and the water layer. Air or water vapor can be present in the nanometer gap.

FIG. 2 (A) Adjacent CNTs covered with an orderly water layer join together as the water layer minimizes the overall surface area; when there is air or water vapor in the nanometer gap, adjacent CNTs do not readily come closer. (B) Dehydration in the presence of $HClSO_3$ leads to a more orderly and densely packed water layer with increased charge separation, which in turn induces more charge separation on the CNT surface. Increased charge separation results in increased attractive force between CNTs. Thinning of the orderly water layer further brings adjacent CNTs closer and densifies the CNT film or sheet (only one molecular layer is shown for brevity). Densification could also be facilitated during dehydration when air or water vapor in the nanometer gap is removed, resulting in a vacuum gap.

FIG. 3 (A) Chlorosulfonic acid ($HClSO_3$) molecules are highly polar with a partial positive charge on the "H" end and a partial negative charge on the "O" end; (B) After high temperature annealing, CNTs become more polarized with charge separation. When treated with $HClSO_3$, an orderly layer of $HClSO_3$ molecules forms around individual CNT surfaces. Because of the high polarity of $HClSO_3$, CNTs inside the layer becomes more polarized and the attractive force increases dramatically between adjacent CNTs, resulting in densification of CNT sheet. Subsequently washing with $H_2O$ could lead to the orderly water layer structure as shown in FIG. 2B.

FIG. 4 Scanning electron microscopy (SEM) image of pristine CNT sheets (A) showing the presence of considerable amounts of what is most likely amorphous carbon attached to individual CNTs; (B) after annealing at 1000° C. for 4 h, showing very little particle or amorphous carbon remaining.

FIG. 5 Photographs of free-standing and flexible CNT films (A) before and (B) after densification process, showing dark color and shiny metallic characteristic, respectively.

FIG. 6 SEM images of CNT sheet after the densification process in the presence of $HClSO_3$ (A) magnification 80,000×; (B) magnification 320,000× showing extensive bundling and visible pores <10 nm in size.

FIG. 9 EMI shielding effectiveness of (A) CNT films with different treatment process and (B) densified CNT film with different thickness at X-band frequency range.

FIG. 10 (A) Before and after high temperature and humidity treatment and (B) Before and after strong acid and alkali soak. The EMI SE is nearly unchanged after storage in harsh environment for 30 days, demonstrating chemical and structural stability of densified CNT film.

DETAILED DESCRIPTION

Figure 7:
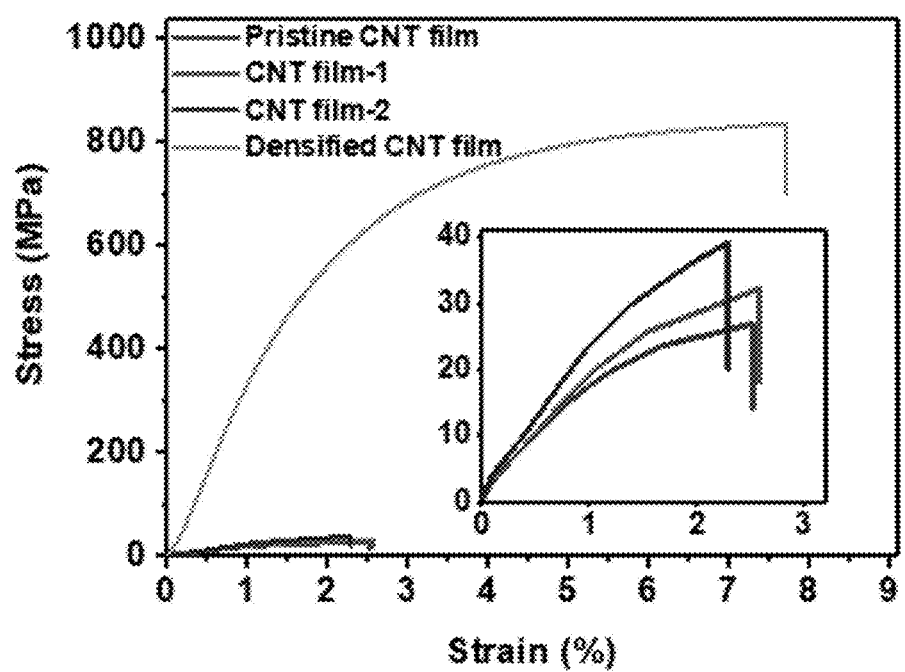
FIG. 7 Representative stress-strain curves of densified CNT film with tensile strength >800 MPa; inset is the typical stress-strain curves of CNT films without densification treatment, showing low tensile strength.

As used herein, an "inert atmosphere" refers to a chemically inactive gaseous medium having an inert gas. Inert gases may be selected from nitrogen and noble gases including helium, neon, argon, krypton, and xenon. The inert atmosphere may be doped with small amounts of hydrogen gas to react any trace amounts of oxygen present in the atmosphere.

Without wishing to be bound to any particular theory, the following description identifies various facets of the invention and its uses.

CNTs are composed of aromatic structures and each individual CNT can be viewed as a gigantic molecule. According to molecular orbital theory, one 2p orbital from each carbon atom participates in the recombination of 2p orbitals to form molecular $\pi$ orbitals. Each molecular $\pi$ orbital has a unique number of nodes. The higher the energy level, the more nodes the $\pi$ orbital has. As electrons fill up the $\pi$ orbitals, they will be in $\pi$ orbitals with more and more nodes. The nodes can be interpreted as "+" or "−" in electron cloud distribution. In essence, electrons in higher energy $\pi$ orbitals can be viewed as localizing more closely around some carbon atoms while staying away from other carbon atoms. The result is, even though a CNT molecule as a whole is charge neutral, there is partial positive charge around some carbon atoms while there is partial negative charge around the other carbon atoms across the CNT surface. This non-uniform electron density distribution (albeit very small) can explain the difference in $^{13}C$ NMR chemical shifts of aromatic molecules (e.g. pyrene). Recent spectroscopic evidence also indicates non-uniform electron density distribution in CNT and graphene materials. Non-uniform electron density distribution across CNT surface can be interpreted as having strong dipoles or alternating positive and negative charges (or partial charges) (FIGS. 1A and 1B). Because of this charge separation, CNTs wound in CNT sheets would interact preferentially with polar molecules such as water molecules, behaving as a hydrophilic substance, even though there is no hydrophilic chemical functional group to interact with water molecules on a perfect CNT surface.

The presence of amorphous carbon disrupts the orderly charge separation along the CNT surface. Amorphous carbon also contributes to the hydrophobicity of CNT by keeping air pockets near the CNT surface. Removal of amorphous carbon content in pristine CNT sheet results in cleaner, more crystalline CNTs with fewer structural defects and a considerably higher degree of uniformity in terms of tube diameter, surface smoothness, and crystallinity.

In such a purified CNT sheet, an adsorption layer of water forms around individual CNTs, establishing a nanometer gap between CNT surfaces and the water layer (FIG. 1C). Air or water vapor exists in this nanometer gap space. Treating purified CNT sheet with concentrated $H_2SO_4$ further stabilizes the adsorption of the water layer. It is envisioned that the water layer becomes more orderly due to the kosmotropic effect of $SO_4^{2-}$. The water layer becomes increasingly ordered as it nears the CNT surface. Adjacent CNTs join together through water layer surface minimization (FIG. 2A). However, as air or water vapor occupies the nanometer gap, resistance likely arises as CNTs draw closer toward one another.

Subsequent treatment with chlorosulfonic acid ($HClSO_3$) thins and polarizes the orderly water layer even further, which in turn relays the electrical field change to further enhance CNT charge separation. Consequently, attractive forces between adjacent CNTs increases dramatically to densify CNTs in the CNT sheet (FIG. 2B). It is also likely that water vapor in the nanometer gap is gradually removed, resulting in a vacuum gap that further facilitates the densification of the CNTs. The resulting CNT sheet becomes more robust with higher tensile strength and does not lose individual CNTs.

Another possibility is that concentrated $H_2SO_4$ forms a layer around individual CNTs within the purified CNT sheet. Upon rinsing with water, an orderly water layer forms around CNTs. When treated with $HClSO_3$, the water layer becomes thinner and more polarized. Such polarization in water layer leads to greater charge separation within the CNT. Consequently, CNTs have more attractive force toward each other which brings CNTs closer together, densifying the CNTs into a CNT sheet.

A further possibility is that $HClSO_3$ (molecules with strong dipole, FIG. 3A) completely removes the orderly water layer near the CNT surface, and an orderly layer of $HClSO_3$ subsequently forms very close to the CNT surface (FIG. 3B). Because $HClSO_3$ is highly polar, a layer of $HClSO_3$ causes enhanced charge separation in individual CNTs. With more attractive force toward each other, CNTs densify to form a durable CNT sheet with improved tensile strength.

During the FCCVD process to produce CNT sheets, CNT growth in the furnace at high temperature (1000° C. to 1200° C.) happens very fast (typically within seconds) and the as-grown CNTs are pulled out of the furnace simultaneously. Amorphous carbon inevitably forms during this process. There are also likely many structural defects in as-grown CNTs. Once CNTs are wound and pressed into CNT sheets, much of the amorphous carbon is embedded in the sheet structure (FIG. 4A).

Amorphous carbon and structural defects in CNT sheets present a few challenges: 1) the physical strength of the film is compromised due to weaker adhesion/bundling between individual CNTs; 2) CNT loss can occur due to CNT adhesion to other surfaces; 3) CNT surface deposition of polymers or small molecules becomes difficult due to micro air pockets present in the sheet structure; and 4) the quality of CNT sheet is difficult to control, as amorphous carbon and structural defects readily affects CNT surface properties. It is therefore necessary to purify the CNTs by removing amorphous carbon and mending structural defects in the CNTs.

Annealing CNT sheet at 1000° C. or above under an inert atmosphere for 1 to 8 h can effectively remove amorphous carbon from pristine CNT sheets and results in CNTs with considerably smoother surfaces (FIG. 4B) and possibly improved crystallinity. The annealing process presumably also contributes to the mending of structural defects in CNTs, and thus CNTs become considerably more uniform within the CNT sheet. In some embodiments, the annealing temperature can be between 600 and 1400° C. In some embodiments, the annealing temperature can be between 800 and 1200° C. The duration of annealing process can be reduced at higher temperatures and extended at lower temperatures.

Based on molecular orbital theory and spectroscopic evidence, charge separation exists in CNT molecules. Greater charge separation corresponds to higher CNT hydrophilicity. One method to increase charge separation is to raise the energy level of π electrons in a CNT molecule. Because there are a very large number of π orbitals, the energy gap between highest occupied molecular orbital (HOMO) and lowest unoccupied molecular orbital (LUMO) is relatively small. Therefore, heat treatment of a CNT molecule can result in π electrons jumping from HOMO to LUMO. As the higher energy level LUMO has more nodes, more π electrons in the LUMO corresponds to greater charge separation in the CNT molecule. Therefore, purified CNT sheets are highly hydrophilic after annealing under inert atmosphere and can be used for water filtration with a large flux rate. However, such a CNT sheet is prone to rupture under shear or pressure. When such a sheet is pressed against a hard surface such as Teflon, visible CNT loss is generally observed.

Physical means to densify CNT sheets are not effective when CNT sheets are thinner than 50 μm. Loss of CNTs is also a problem due to CNTs adhering upon pressing to a flat surface. The length of CNTs in a CNT sheet also varies, which can have a significant impact on how CNTs interact with each other. When the adhesion force between CNTs is not sufficiently strong, CNT loss during process handling becomes more severe. A molecular approach is required to prepare CNT sheets that are physically robust and durable without the use of polymer binder and mechanical force.

With the removal of surface amorphous carbon and the elevated charge separation resulting from high temperature treatment, annealed CNT molecules have strong attraction toward polar molecules such as water. A perfect CNT molecule does not have any surface functional groups to interact with water molecules. Yet it is reasonable to envision that as more water molecules get closer to the CNT surface, hydrogen bonding among them leads to the formation of a layer of orderly water, establishing a gap between the orderly water layer and the CNT surface. When CNT charge separation is higher, the gap is most likely smaller and the water layer is thicker and more orderly. As a result, heat-treated CNT sheets appear highly hydrophilic. Over time as energy dissipates, the degree of charge separation decreases and the attractive forces between the CNT and water layers subsequently drops. Consequently, the water layer becomes less orderly and moves further away from CNT surface, increasing the gap size. As water molecules move away from the CNT surface, the CNT surface appears more hydrophobic.

Elevated charge separation from high temperature treatment alone is not sufficient to bring CNTs close enough for densification. Other highly polar molecules (such as molecules more polar than water) used to form an orderly layer "wrapping" around the CNT surface, can further enhance charge separation in the CNT. As a result, annealed CNT sheets treated with protic acids, including $H_2SO_4$ or $H_3PO_4$, appear slightly more hydrophilic. Elevating the temperature of the CNT sheets in protic acids may reduce the time for effective treatment. In some embodiments, it may be for a period of at least 30 minutes. However, likely due to the buffering capacity from the orderly water layer adjacent to the CNT surface, charge separation increases achieved during concentrated $H_2SO_4$ or $H_3PO_4$ treatment is insufficient to densify CNTs into durable CNT sheets.

$HClSO_3$ is highly hygroscopic and polar. When a CNT sheet is treated with $HClSO_3$, the water layer is gradually thinned and removed and the formation of a layer of $HClSO_3$ around individual CNT surfaces induces a substantial enhancement of charge separation in the CNTs. As $HClSO_3$ is slowly removed upon heating, individual CNTs are brought closer due to increased attractive force. As a result, CNT densification leads to the formation of a durable and robust CNT sheet. Densified CNT sheets appear silvery gray, unlike dark pristine CNT sheets (FIG. 5). SEM images indicate that the pore sizes in the densified CNT sheets decreases to 10 nm or smaller, with uniform bundling (FIG. 6). Extensive conjugation between densified CNTs results in further stabilization of charge separation across the CNT sheet. Extensive charge separation could be responsible for the metallic luster of the densified CNT sheet.

Compared to pristine CNT sheets of similar areal density, densified CNT sheets have improved tensile strength of 300~800 MPa (vs. 20~120 MPa for pristine CNT sheets) (FIG. 7). Tensile strength and other properties can vary depending on pristine CNT quality, individual CNT diameter (from ca. 2 nm to ca. 50 nm) and diameter distribution, amorphous carbon content and areal density (from ca. 2 $g/m^2$ to 25 $g/m^2$). In some instances, weight loss after annealing can be ca. 30%.

Figure 8:
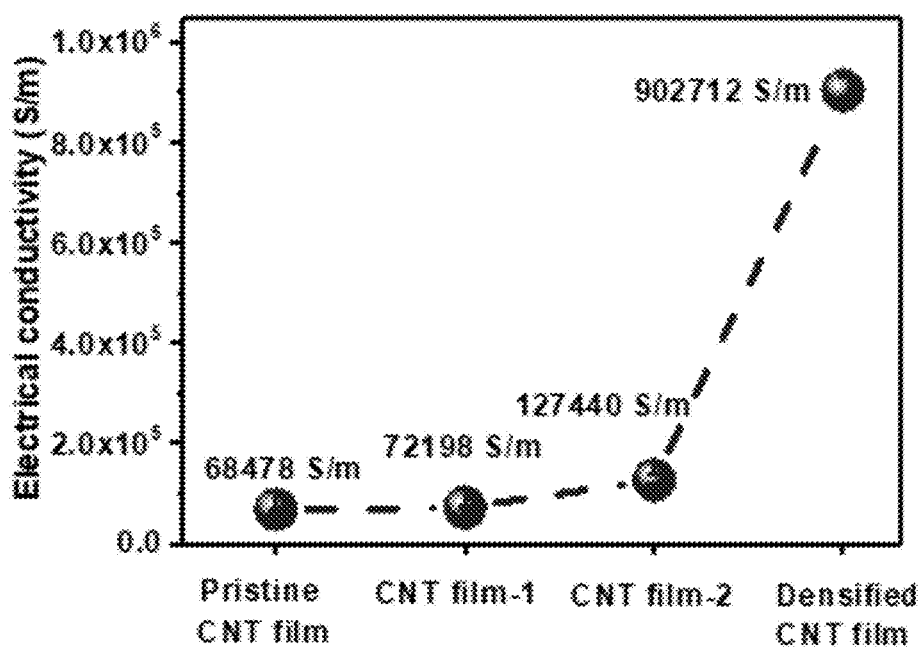
FIG. 8 Electrical conductivity of CNT films, showing a dramatic increase in conductivity after treatment with chlorosulfonic acid for densification.

Densified CNT sheets are also much thinner and more electrically conductive, with conductivity reaching $1 \times 10^6$ S/m (from ca. $5 \times 10^4$ S/m in pristine CNT sheets) (FIG. 8) and $R_{sq}<0.5\Omega$. Impurities such as amorphous carbon severely inhibit the densification between individual CNTs, leading to limited increase in mechanical strength, electrical conductivity and EMI shielding performance. For example, pristine CNT films can undergo some densification when treated directly with chlorosulfonic acid. But the conductivity of the resulting film is typically $<5 \times 10^5$ S/m with tensile strength of ca. 100 MPa. Densified CNT sheets (1.85 μm fil thickness) also have enhanced EMI shielding effectiveness in the X band (8 GHz to 12.5 GHz) (51.2 dB vs 35 dB in pristine CNT sheets) (FIG. 9). The EMI shielding effectiveness of densified CNT films further increases to 73.3 dB, 84.5 dB and 101.4 dB (i.e., >99.99999999% of the incident electromagnetic waves can be blocked) with film thickness of 3.98 μm, 6.36 μm and 14.67 μm, respectively.

Reliability of EMI shielding performance is crucial to ensure the normal operation of electronic devices for long period, especially in harsh environment such as high temperature/high humidity and acid/alkali circumstance. The EMI shielding effectiveness of densified CNT film after treatment in 85° C. and 85% relative humidity (RH) for up to 30 days is almost identical to that before treatment (FIG. 10 A), suggesting high stability, which far outperforms that of MXene-based shielding materials. The EMI shielding effectiveness of densified CNT film after respectively being stored in sulfuric acid (pH=0) and sodium hydroxide aqueous solution (pH=14) for one month is almost unchanged (FIG. 10 B), indicating the strong corrosion resistance of densified CNT sheets. These intriguing characteristics cannot be achieved by traditional metal-based materials. Thus, polymer-free densified CNT sheets represent a critical breakthrough in the preparation of EMI shielding materials towards applications in wearable smart electronics and 5G communication devices.

Densified CNT sheets are hydrophilic and can be used as water filtration membranes. Depending on the sheet thickness and pore sizes, flux rates can reach 451 L/($m^2 \cdot h$) at 0.1 MPa, 1068.4 L/($m^2 \cdot h$) at 0.2 MPa, 2693.8 L/($m^2 \cdot h$) at 0.3 MPa, and 2863.7 L/($m^2 \cdot h$) at 0.4 MPa for pure water. When used to filter a bovine serum album (BSA) solution (1 g/L), densified CNT sheets with smaller pores have achieved greater than 50% molecular weight cutoff, indicating their effectiveness in removing contaminants from water.

Densified CNT sheets have excellent bare membrane permeance for various gases, e.g., 293,000 GPU for $N_2$, 269,000 GPU for $O_2$, and 672,000 GPU for He. Bare membrane selectivity suggests Knudsen flow through the membrane. Thus, densified CNT sheets are useful for the removal of particulates from air and other gases.

Examples

A raw thin CNT sheet (13.09 mg, areal density ~6 $g/m^2$, size 5 cm×5 cm) from FCCVD process was heated at 1000° C. in a tube furnace under an inert atmosphere (2% $H_2$ 98% $N_2$) for 4 hours, cooled to ambient temperature under inert atmosphere, and weighed (10.61 mg, 19% weight loss). The CNT sheet was stored in air for about 3 weeks before it was placed in an Erlenmyer flask and treated with concentrated $H_2SO_4$ drops (21.3 mg, 11.6 μL) via a pipette tip. The flask was capped with a ground stopper and placed on a hot plate at 110° C. for 24 hours. The CNT sheet was cooled to ambient temperature and rinsed with deionized (DI) $H_2O$ (5×) and dried in air for 3 days before it was weighed (10.43 mg). The dried CNT sheet was placed in an Erlenmyer flask and treated with $HClSO_3$ (62.58 mg, 35.7 μL) via a pipette tip. The flask was capped with a ground stopper and kept for 1 hour at ambient temperature, then heated at 110° C. for 96 hours. Upon cooling to ambient temperature, the CNT sheet was rinsed with DI $H_2O$ (5×) and dried in air (11.76 mg). The sheet appeared soft with a silver sheen. When pressed against polyethylene surface and PTFE surface, no CNT loss was visible, indicating the densification of CNTs in the sheet.

A raw thin CNT sheet (11.01 mg, areal density ~6 $g/m^2$, size 5 cm×5 cm) from FCCVD process was heated at 1000° C. in a tube furnace under inert atmosphere (2% $H_2$ 98% $N_2$) for 4 hours, cooled to ambient temperature under an inert atmosphere and weighed (7.96 mg, 27.7% weight loss). The CNT sheet was immediately placed in an Erlenmyer flask and treated with concentrated $H_2SO_4$ drops (16.0 mg, 8.8 μL) via a pipette tip. The flask was capped with a ground stopper and placed on a hot plate at 110° C. for 24 hours. The CNT sheet was cooled to ambient temperature and rinsed with DI $H_2O$ (5×) and dried in air for 3 days before it was weighed (8.13 mg). The dried CNT sheet was placed in an Erlenmyer flask and treated with $HClSO_3$ (96.24 mg, 55 μL) via a pipette tip. The flask was capped with a ground stopper and kept for 1 hour at ambient temperature, then heated at 110° C. for 96 hours. Upon cooling to ambient temperature, the CNT sheet was rinsed with DI $H_2O$ (5×) and dried in air (8.97 mg). The sheet appeared soft with a silver sheen. When pressed against polyethylene surface and PTFE surface, no CNT loss was visible, indicating the densification of CNTs in the sheet.

A raw thin CNT sheet (12.03 mg, areal density ~6 $g/m^2$, size 5 cm×5 cm) from FCCVD process was heated at 1000° C. in a tube furnace under an inert atmosphere (2% $H_2$ 98% $N_2$) for 4 hours, cooled to ambient temperature under an inert atmosphere and weighed (8.26 mg, 31.3% weight loss). The CNT sheet was immediately placed on a Teflon block substrate and treated with solid $SO_3$ $NEt_3$ complex (12.15 mg). The solid complex was spread across the CNT sheet. Subsequently, the CNT sheet on the Teflon block was placed in a vacuum oven at 100° C. for 24 hours. The CNT sheet was cooled to ambient temperature and rinsed with DI $H_2O$ (5×) and dried in air for 3 days before it was weighed (8.35 mg). The dried CNT sheet was placed in an Erlenmyer flask and treated with $HClSO_3$ (100.2 mg, 57.2 μL) via a pipette tip. The flask was capped with a ground stopper and kept for 1 hour at ambient temperature, then heated at 110° C. for 96 hours. Upon cooling to ambient temperature, the CNT sheet was rinsed with DI $H_2O$ (5×) and dried in air (9.16 mg). The sheet appeared soft with a silver sheen. When pressed against polyethylene surface and PTFE surface, no CNT loss was visible, indicating the densification of CNTs in the sheet.

Because the densified CNT sheets are resistant to fouling and highly efficient for water filtration, water filters from densified CNT sheets are suitable biopharma processing including fermentation processes, as linings for vessel reactors and containers, membranes and coatings. They are also useful for ultra-purification of water needed in many biopharma processing.

One embodiment of the subject matter provides a method to densify a CNT sheet or film without mechanical compression. After annealing at high temperature, the CNT sheet is immediately treated with a concentrated acid such as phosphoric acid or sulfuric acid at elevated temperature. Upon rinsing with water, the resulting sheet is dried in air and further densified in the presence of chlorosulfonic acid ($HClSO_3$) at elevated temperature. The densified CNT sheet is hydrophilic, mechanically robust, durable, and does not adhere to other solid surfaces such as Teflon, Nylon films and metal block surfaces. No CNT loss is visible from the densified CNT sheet after being pressed against Teflon or polypropylene surfaces. Densified CNT films or sheets appear silvery and have increased conductivity (between $5\times10^5$ S/m and $1\times10^6$ S/m).

In a further embodiment, a purified CNT sheet is stored in air for an extended period of time after annealing and is then treated with concentrated acid such as phosphoric acid or sulfuric acid at elevated temperature. Upon rinsing with water, the resulting sheet is dried and further densified in the presence of $HClSO_3$ at elevated temperature to produce a silvery, durable CNT sheet.

In another embodiment, a purified CNT sheet is immediately treated with $SO_3 NEt_3$ complex at elevated temperature after annealing. Upon rinsing with water, the resulting sheet is dried and further densified in the presence of $HClSO_3$ at elevated temperature to provide a densified CNT sheet with improved tensile strength and electrical conductivity.

What is claimed is:

1. A method for producing a densified carbon nanotube (CNT) sheet, comprising contacting a CNT sheet with $HClSO_3$;
   heating the CNT sheet resulting in the densified CNT sheet having an improved electroconductivity or tensile strength;
   wherein the densified CNT sheet has:
       an electroconductivity of greater than $5\times10^4$ S/m, or
       a tensile strength greater than 120 MPa.

2. The method of claim 1, further comprising:
   inserting a CNT sheet into an inert atmosphere;
   heating the CNT sheet to an elevated temperature; and
   cooling the CNT sheet to an ambient temperature.

3. The method of claim 2, further comprising:
   contacting a CNT sheet with a solution comprising a protic acid;
   rinsing the CNT sheet with a volume of protic solvent; and
   removing the protic solvent.

4. The method of claim 2, further comprising:
   melting $SO_3NEt_3$ complex on a CNT sheet;
   rinsing the CNT sheet with a protic solvent;
   removing the protic solvent.

5. A densified CNT sheet produced by the method of claim 1.

6. A densified CNT sheet produced by the method of claim 2.

7. A densified CNT sheet produced by the method of claim 3.

8. A densified CNT sheet produced by the method of claim 4.

9. A method of shielding an article from electromagnetic radiation, comprising covering an article with a densified CNT sheet of claim 5.

10. A method of filtering a liquid, comprising passing the liquid through the densified CNT sheet of claim 5.

11. A method of filtering a gas, comprising passing the gas through the densified CNT sheet of claim 5.

12. A method of protecting a surface from corrosion, comprising covering a surface of an object with the densified CNT sheet of claim 5, and contacting the surface with a corrosive material.

13. The method of claim 12, wherein the corrosive material is a protic acid solution or alkaline solution.

14. A method of protecting a surface from fouling, comprising covering a surface of an object with the densified CNT sheet of claim 5, and contacting the surface with a fouling material.

15. The method of claim 14, wherein the fouling material is a fermentation solution or a biological culture.

16. The method of claim 14, wherein the fouling material is a heat exchange fluid.

17. The method of claim 2, wherein the elevated temperature is between about 800 and about 1200° C.

18. The method of claim 2, wherein the inert atmosphere comprises 1% to about 5% hydrogen.

19. The method of claim 2, wherein the densified CNT sheet has an electroconductivity of greater than $5\times10^5$ S/m or a tensile strength greater than 300 MPa.

20. The method of claim 3, wherein the densified CNT sheet has an electroconductivity of greater than $5\times10^5$ S/m or a tensile strength greater than 300 MPa.

* * * * *